US010548469B2

(12) United States Patent
Weiss et al.

(10) Patent No.: US 10,548,469 B2
(45) Date of Patent: *Feb. 4, 2020

(54) ORAL MONITOR

(71) Applicant: Location Labs, Inc., Emeryville, CA (US)

(72) Inventors: Andrew Weiss, San Ramon, CA (US); Scott Hotes, Berkeley, CA (US)

(73) Assignee: Location Labs, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/244,597

(22) Filed: Jan. 10, 2019

(65) Prior Publication Data

US 2019/0142260 A1 May 16, 2019

Related U.S. Application Data

(63) Continuation of application No. 14/479,591, filed on Sep. 8, 2014, now Pat. No. 10,178,946.

(51) Int. Cl.
| | | |
|---|---|---|
| *A61B 1/05* | (2006.01) | |
| *A61B 1/24* | (2006.01) | |
| *A61C 19/04* | (2006.01) | |
| *A61B 5/145* | (2006.01) | |
| *A61B 5/00* | (2006.01) | |
| *A61C 7/14* | (2006.01) | |

(52) U.S. Cl.
CPC ............ *A61B 1/24* (2013.01); *A61B 5/14507* (2013.01); *A61B 5/14532* (2013.01); *A61B 5/4845* (2013.01); *A61B 5/682* (2013.01); *A61C 7/14* (2013.01); *A61C 19/04* (2013.01)

(58) Field of Classification Search
CPC ..... A61B 1/24; A61B 5/14507; A61B 5/4845; A61B 5/14532; A61B 5/682; A61C 19/04; A61C 7/14
See application file for complete search history.

(56) References Cited

U.S. PATENT DOCUMENTS

| | | | |
|---|---|---|---|
| 527,037 | A | 10/1894 | Funk |
| 3,382,781 | A * | 5/1968 | Hamilton ........... A61B 1/00142 396/16 |
| 3,837,922 | A | 9/1974 | Ng et al. |
| 3,861,397 | A | 1/1975 | Rao et al. |
| 3,941,135 | A | 3/1976 | Von Sturm et al. |

(Continued)

OTHER PUBLICATIONS

Awford, "Pinhole camera takes photos from inside a man's mouth"—Daily Mail—Aug. 14, 2014 (Year: 2014).*

(Continued)

*Primary Examiner* — Philip P. Dang
(74) *Attorney, Agent, or Firm* — Dovas Law, P.C.

(57) ABSTRACT

An oral monitoring system is provided. The oral monitoring system includes one or more cameras configured for installation in a mouth for capturing images. A memory is configured for storing images. One or more processors are configured to process images captured by the one or more cameras, and a wireless transmitter is configured to transmit data corresponding to the captured images. A chemical sensor is further provided and the wireless transmitter is further configured to transmit data corresponding to substances detected by the chemical sensor.

38 Claims, 6 Drawing Sheets

(56) References Cited

U.S. PATENT DOCUMENTS

| | | | |
|---|---|---|---|
| 4,294,891 A | 10/1981 | Yao et al. | |
| 4,629,424 A | 12/1986 | Lauks et al. | |
| 5,454,022 A * | 9/1995 | Lee | G01T 1/2928 |
| | | | 348/E5.044 |
| 6,216,024 B1 * | 4/2001 | Weil | A61B 5/0261 |
| | | | 600/353 |
| 6,239,705 B1 | 5/2001 | Glen | |
| 6,276,934 B1 * | 8/2001 | Rakocz | A61B 1/247 |
| | | | 433/29 |
| 6,607,387 B2 * | 8/2003 | Mault | A61B 5/0088 |
| | | | 433/215 |
| 6,719,684 B2 | 4/2004 | Kim et al. | |
| 6,908,307 B2 * | 6/2005 | Schick | A61B 1/24 |
| | | | 396/322 |
| 6,964,567 B2 * | 11/2005 | Kerschbaumer | A61B 1/00041 |
| | | | 433/140 |
| 7,039,453 B2 | 5/2006 | Mullick et al. | |
| 7,057,639 B2 * | 6/2006 | Spoonhower | A61B 1/00016 |
| | | | 348/65 |
| 7,126,303 B2 | 10/2006 | Farritor et al. | |
| 7,193,219 B2 * | 3/2007 | Schick | A61B 5/0088 |
| | | | 250/370.11 |
| 7,410,709 B2 | 8/2008 | Ladisch et al. | |
| 7,985,072 B2 * | 7/2011 | Belikov | A61C 19/063 |
| | | | 433/215 |
| 8,556,625 B2 * | 10/2013 | Lovely | A61B 5/0088 |
| | | | 433/29 |
| 2002/0061495 A1 * | 5/2002 | Mault | A61B 5/0088 |
| | | | 433/215 |
| 2005/0118494 A1 | 6/2005 | Choi | |
| 2007/0019102 A1 | 1/2007 | Nakajo et al. | |
| 2007/0177279 A1 | 8/2007 | Cho et al. | |
| 2008/0009772 A1 * | 1/2008 | Tyler | A61B 5/0492 |
| | | | 600/595 |
| 2009/0190026 A1 | 7/2009 | Chen | |
| 2009/0312817 A1 * | 12/2009 | Hogle | A61B 5/0492 |
| | | | 607/54 |
| 2010/0055570 A1 | 3/2010 | Rodriguez | |
| 2010/0311133 A1 * | 12/2010 | Tokita | H01M 4/90 |
| | | | 435/146 |
| 2011/0046708 A1 | 2/2011 | O'Connor | |
| 2011/0135967 A1 | 6/2011 | Pellissier et al. | |
| 2013/0061798 A1 * | 3/2013 | Ribi | A46B 15/0002 |
| | | | 116/207 |
| 2013/0063550 A1 * | 3/2013 | Ritchey | G16H 40/63 |
| | | | 348/36 |
| 2013/0278396 A1 | 10/2013 | Kimmel | |
| 2014/0002364 A1 * | 1/2014 | Ibsies | G16H 40/63 |
| | | | 345/168 |
| 2014/0178444 A1 * | 6/2014 | Stadler | C07H 15/04 |
| | | | 424/401 |
| 2014/0248574 A1 * | 9/2014 | Yoon | A61C 13/01 |
| | | | 433/8 |
| 2016/0066776 A1 | 3/2016 | Weiss et al. | |

OTHER PUBLICATIONS

A. C. Broussard, Miniature Camera Possibilities, American Society of Orthodontists, Apr. 20-23, 1936 (Year: 1936).*

Awford, "Pinhole camera takes photos from inside a man's mouth"—Daily Mail—Aug. 14, 2014.

A. C. Broussard, Miniature Camera Possibilities, American Society of Orthodontists, Apr. 20-23, 1936.

* cited by examiner

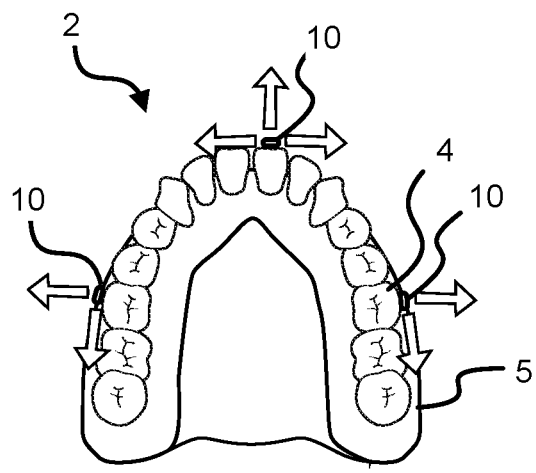
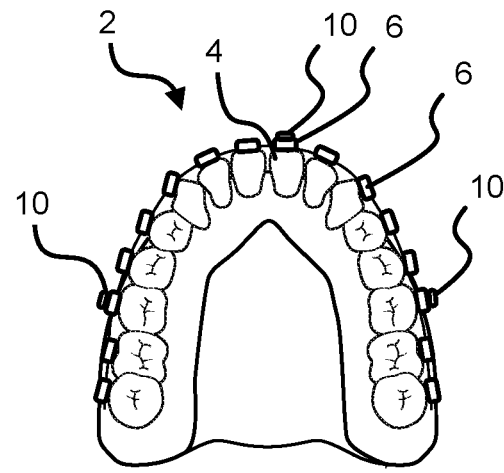
FIG. 3
FIG. 4
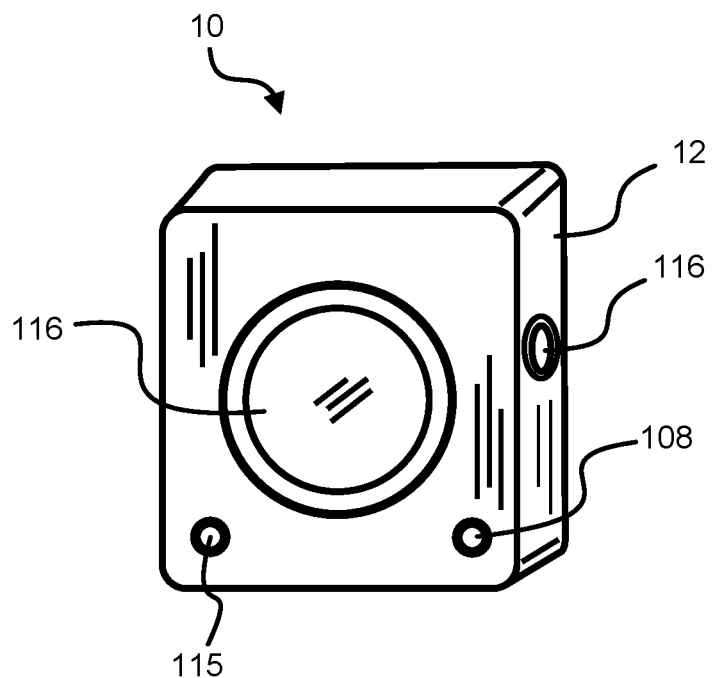
FIG. 5

ORAL MONITOR

CROSS REFERENCE TO RELATED APPLICATION(S)

This application is a continuation of U.S. patent application Ser. No. 14/479,591, filed Sep. 8, 2014, which is incorporated by reference as if fully set forth.

BACKGROUND

Children and adults may make poor choices about the foods they consume and their dental hygiene. They may sneak sugary snacks, eat at times not conducive to health, or neglect to brush their teeth. Particularly, it is difficult for parents to continuously monitor eating and hygiene behavior of their children to ensure that they engage in healthful behavior. Children may not be completely honest to their parents about their eating habits. It may also be difficult for a person to monitor his or her own eating and hygiene behavior. Adults for example may not be honest with themselves about their eating habits.

SUMMARY

This Summary introduces simplified concepts that are further described below in the Detailed Description of Illustrative Embodiments. This Summary is not intended to identify key features or essential features of the claimed subject matter and is not intended to be used to limit the scope of the claimed subject matter.

An oral monitoring system is provided. The oral monitoring system includes one or more cameras configured for installation in a mouth for capturing images. A memory is configured for storing images. One or more processors are configured to process images captured by the one or more cameras, and a wireless transmitter is configured to transmit data corresponding to the captured images.

An oral monitoring method is provided. The method includes providing one or more cameras and installing the cameras in a mouth. One or more images are captured by the one or more cameras, and a processor determines a health state of the mouth or a substance consumed by the mouth based on the one or more images. A notification is transmitted to a user based on the determined health state or substance consumed by the mouth.

In an alternative oral monitoring method, one or more chemical sensors are provided. The one or more chemical sensors are installed in a mouth. The one or more chemical sensors detect a substance, and a processor determines based on the detected substance if a notification is required. A notification is transmitted to a user based on the detected substance.

BRIEF DESCRIPTION OF THE DRAWING(S)

A more detailed understanding may be had from the following description, given by way of example with the accompanying drawings. The Figures in the drawings and the detailed description are examples. The Figures and the detailed description are not to be considered limiting and other examples are possible. Like reference numerals in the Figures indicate like elements wherein:

FIG. 3 shows a plan view of upper teeth in a mouth where oral monitors are mounted to the teeth.

FIG. 4 shows a plan view of upper teeth in a mouth where oral monitors are mounted to braces attached to the teeth.

FIG. 5 is a perspective view of the oral monitor shown in FIGS. 1-4.

DETAILED DESCRIPTION OF ILLUSTRATIVE EMBODIMENT(S)

The terms "a" and "an" as used herein do not denote a limitation of quantity, but rather denote the presence of at least one of the referenced items. Any directional signal such as top, bottom, left, right, upper and lower are taken with reference to the orientation in the various figures.

Figure 1:
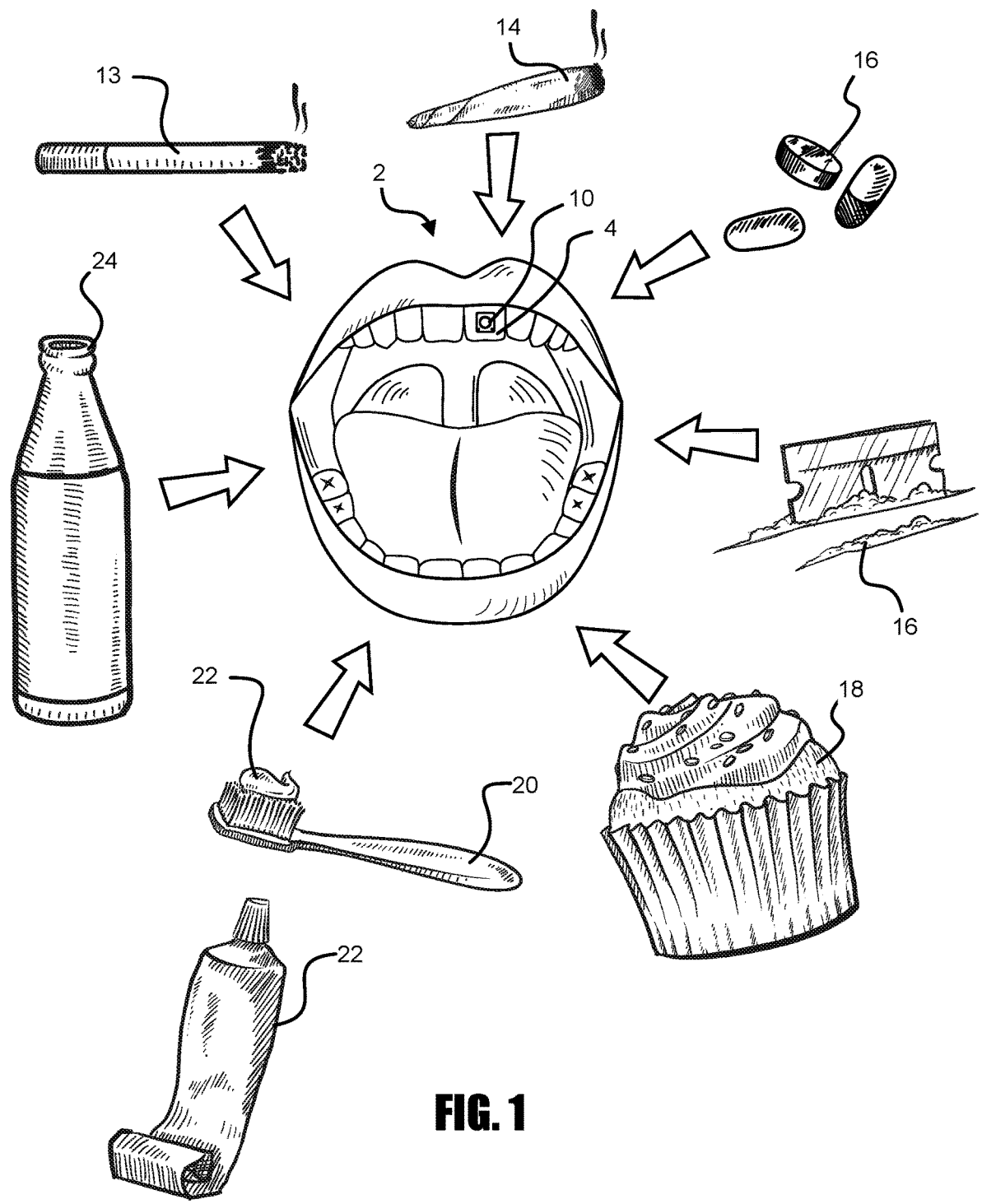
FIG. 1 is a diagram showing edible substances and other consumables in relation to a human mouth with an oral monitoring device installed on a tooth therein.
Figure 2:
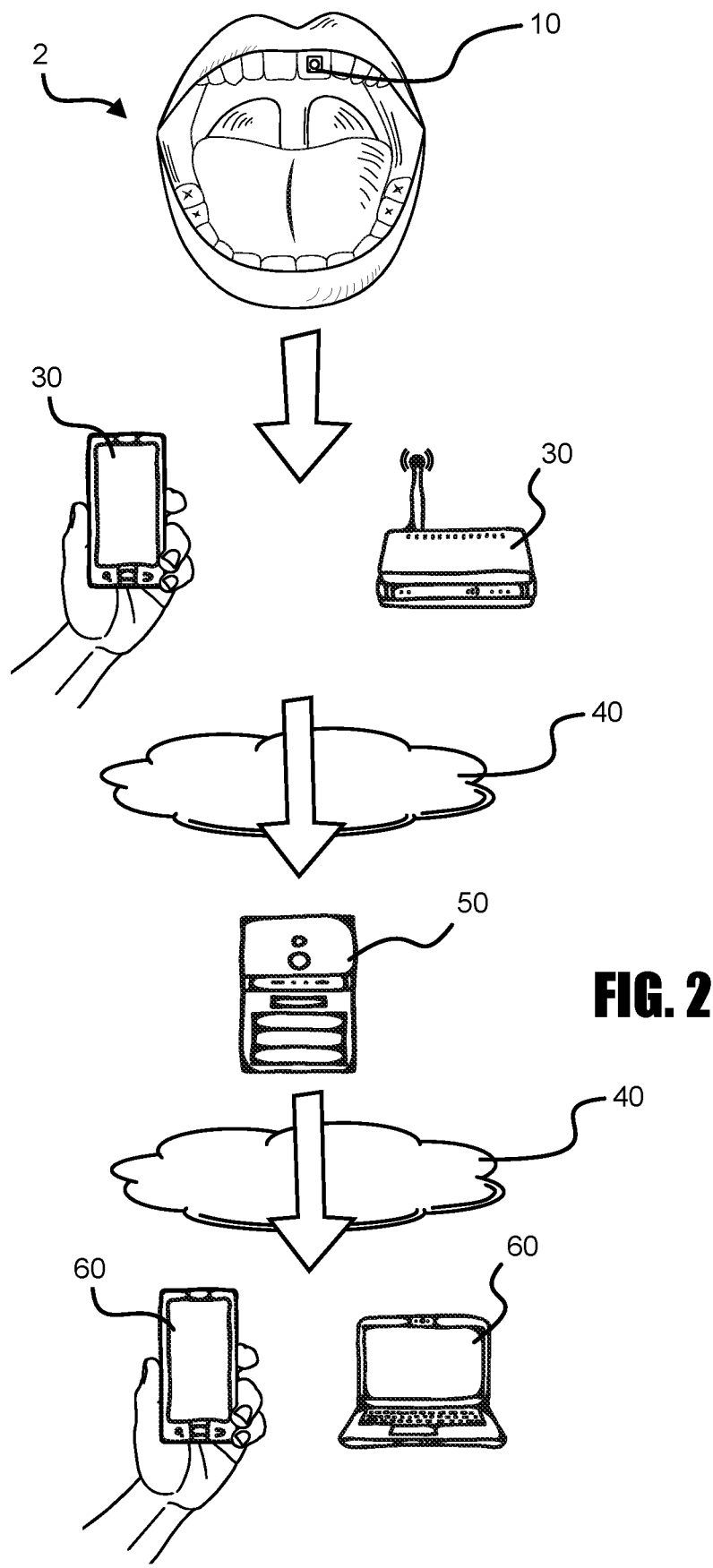
FIG. 2 is a diagram showing data flow from an oral monitoring device in a mouth to various computing devices.

Referring to FIGS. 1-5, oral monitors 10 attached to teeth 4 in the mouth 2 of a human person are shown. Each oral monitor 10 includes a housing 12 which houses hardware 102. While a human mouth is pictured, the oral monitor 10 can alternatively be attached in the mouth of an animal. The oral monitors 10 are configured for adhering to a surface of the teeth 4 as shown in FIGS. 1-3. Alternatively, the oral monitors 10 can be attached to orthodontic devices on the teeth, for example attached to braces 6 adhered to the teeth 4. The hardware 102 includes a camera 116 configured for capturing images and one or more sensors 108 for collecting information to determine the chemical composition of substances which come into contact with the oral monitor 10. Each oral monitor 10 is configured to send data corresponding to collected images and chemical composition of substances to wireless communication devices 30, such as routers, cellular communication devices, or other network connectable communication devices. Alternatively, an oral monitor 10 can send such data to one or more other oral monitors 10 installed in the mouth 2. The oral monitor 10 is configured to determine the occurrence of consumption activities, for example smoking a cigarette 13 or marijuana 14, oral or nasal consumption of legal or illicit drugs 16, eating food 18, brushing teeth with a toothbrush 20 and toothpaste 22, and drinking an alcoholic or non-alcoholic beverage 24.

Figure 6:
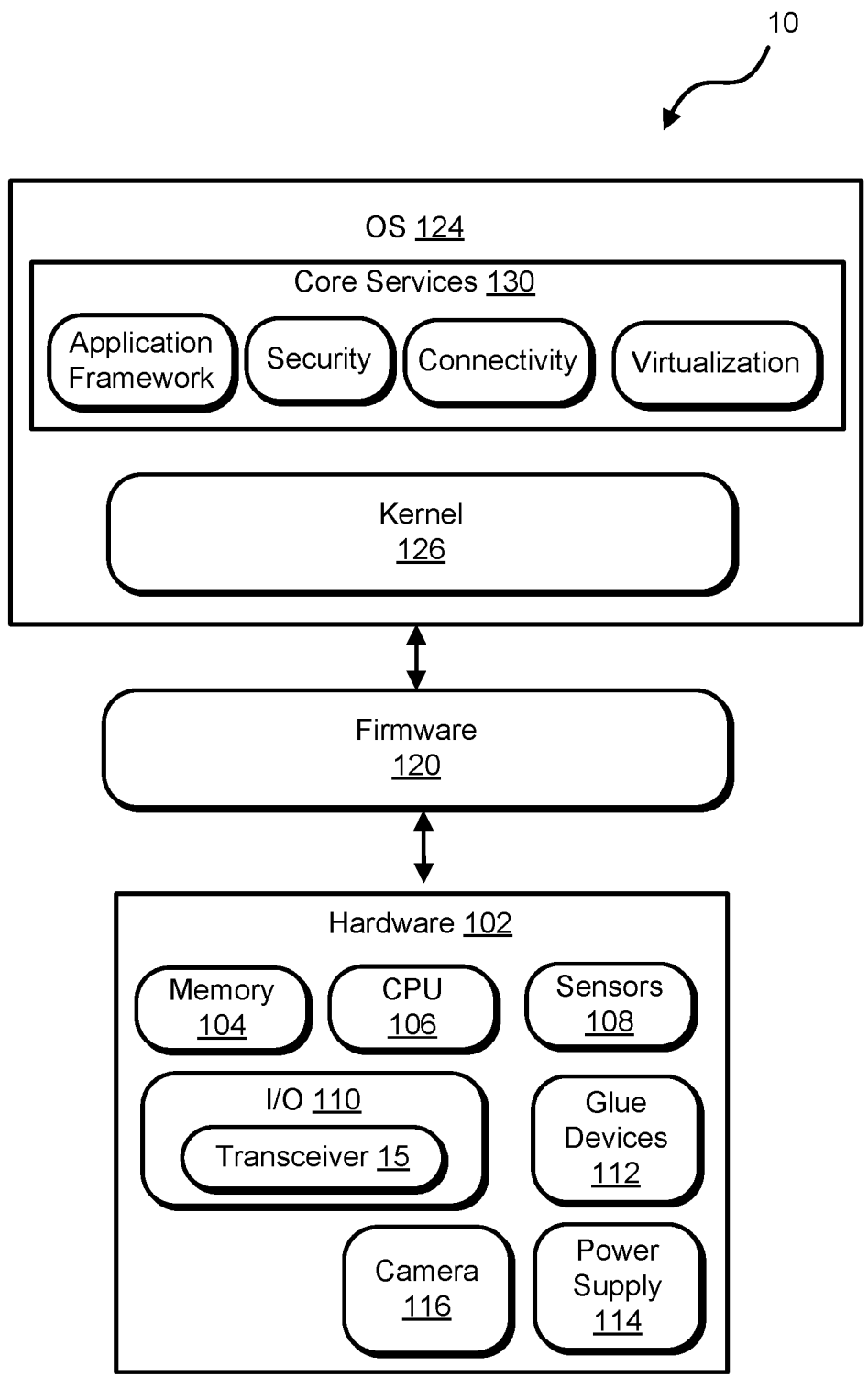
FIG. 6 illustrates an abstract hierarchical operation of the oral monitor of FIGS. 1-5.

FIG. 6 illustrates abstract hierarchical operation of the oral monitor 10 from basic hardware 102 devices to the higher level operating system 124. While the oral monitor 10 is illustrated, similar processor based systems exist in other devices. At the lowest abstraction level is a collection of basic semiconductor hardware 102 devices, typically integrated circuits. Such semiconductor hardware 102 typically includes one or more memory devices ("memory") 104, one or more processors ("CPU") 106, one or more sensors and their support electronics 108 (e.g., chemical sensor), input/output ("I/O") 110 device support (e.g., RF transceivers 15), and glue devices 112 as required to change voltage levels or signal levels and to perform other interfacing as required for proper hardware 102 functionally. A power supply 114 can derive power for the oral monitor 10 from a conventional battery, or alternatively, can derive power from food sugar collected through aperture 115 in the housing 12. Alternatively, the power supply 114 can derive power through body motion.

Still referring to FIG. 6, the next level of abstract hierarchical progression is firmware 120, if required. Firmware 120 is useful for enabling upgrading of the oral monitor 10 by storing, in non-volatile memory, settings such as model numbers, version numbers, and controlling bits which establish a set of functions and limit or restrict the oral monitor's capabilities.

Moving up the abstract hierarchical progression from the firmware 120 is an operating system 124. The operating system 124 provides a set of core software programs that manage the semiconductor hardware 102 and firmware 120 and implements common services required for application software. The operating system 124 includes a low-level "kernel" routine 126 that handles basic software integration to the firmware 120 and hardware 102 to implement underlying functions. The core services 130 are software functions that support the on-board services of the oral monitor 10. The core services 130 can include software routines that support and enable the application framework, system security, connectivity, and virtualization.

The memory 104 of a particular oral monitor 10 is configured for storing images captured by the camera 116 of the particular oral monitor 10 or images captured by one or more other cameras 116 from other oral monitors 10 located in the mouth 2. The camera 116 can capture still images or motion video including a plurality of images taken at a particular frame rate. The CPU 106 is configured to process captured images, and a transceiver 15 is configured to transmit data corresponding to such images to wireless communication device 30 such as a cellular communication device (e.g., smartphone), wireless enabled personal computer, or wireless router. A chemical sensor 108 is configured to detect food sugar. The CPU 106 further is configured to process food sugar information collected by the chemical sensor 108, and the transceiver 15 is configured to transmit data corresponding to such food sugar information to a wireless communication device 30. The CPU 106 is configured to perform activity classification and state classification by implementing a classifier against the captured image data and/or the collected chemical sensor data. The oral monitor 10 has wireless network communication capability for example wireless Ethernet (e.g., IEEE 802.11 "Wi-Fi™" protocol) and Bluetooth™ enabling communication with wireless communication devices 30 to allow for transmission data from the oral monitor 10.

The housing 12 of each oral monitor 10 can be adhered to the surface of a tooth 4 using a suitable orthodontic adhesive. Alternatively, the housing 12 can be attached to an orthodontic apparatus such as braces 6. FIGS. 3 and 4 show a plan view looking up at the upper teeth where one oral monitor 10 is mounted to a central incisor tooth 4, and two other oral monitors 10 are mounted to first molar teeth 4 on opposite sides of the mouth 2. The cameras 116 face laterally and outwardly as shown by arrows in FIGS. 3 and 4 to capture images of objects and substances entering the mouth and objects and substances within the mouth, and to capture images of the condition of the teeth 4 and gums 5.

The CPU 106 can determine whether teeth have been brushed based on images captured by the camera 116 and/or data provided by the chemical sensor 108. The CPU 106 can implement software to apply a classifier to captured images and/or data provided by the chemical sensor 108 to determine if the tooth brushing has occurred. The CPU 106 can further determine based on images from a side camera 116 directed at the teeth an amount of plaque on the teeth 4, a formation of a cavity in a tooth 4, a tooth abscess, or other dental or medical anomaly in the mouth. It can further be determined based on the images when a threshold amount of plaque has accumulated on one or more teeth. Such determinations can be made for example by implementing a classifier. A notification can be transmitted by the transceiver 15 responsive to determining a medical or dental anomaly or responsive to determining a threshold amount of plaque has accumulated.

Consumption activities can be determined by the CPU 106 for example by application of a classifier based on images captured by cameras 116 and/or data provided by a chemical sensor 108, and a corresponding report can be generated. Determined consumption activities can include for example an indication of a type of food eaten using the mouth 2. In an exemplary implementation, a camera 116 can take a video showing eating activity, and a classifier running on the CPU 106 can determine that activity is a food eating engagement. A chemical sensor 108 can detect the amount of sugar in the food, and if the sugar exceeds a particular level, the food is classified as a snack item. The duration and time of day can be determined for the eating activity, and the number of eating engagements per day can be determined. This activity information can be transmitted to the person in whose mouth the oral monitor 10 is installed or a parent of a child in whose mouth the oral monitor 10 is installed. Such monitored person or parent can therefore know the number of times during the day that the monitored person is engaged in eating, and the number of these engagements that involved the consumption of snack food.

Smoking activity can be determined and reported based on images from the camera 116 and/or chemical data from a chemical sensor 108. Smoking activity can include tobacco smoking, marijuana smoking, or smoking of other substance, legal or illicit. The chemical sensor 108 can be configured to detect legal or illicit drugs smoked, ingested or consumed in any manner, orally or nasally, which results in a chemical change within the mouth 2. Such drugs can include a mind altering substance such as caffeine, nicotine, alcohol, cocaine, lysergic acid diethylamide ("LSD"), methylenedioxymethamphetamine ("MDMA"), ketamine, or methamphetamine ("Meth"). A report can be generated including an indication of the detected drug. Information regarding smoking, drug use, or alcohol consumption can be transmitted to a parent of a child in whose mouth the oral monitor 10 is installed.

Sugar from foods in the mouth 2 can be collected through aperture 115 in the housing 12. The power supply 114 can implement a chemical converter to produce electricity from the collected sugar to power the oral monitor 10.

Processing of image and sensor data and report generation as described above can be performed by one or more processors ("CPU") 106 on an oral monitor 10. In such case a report based on processed image or sensor data can be transmitted to a wireless communication device 30, which device 30 can correspond to a person in whose mouth 2 the oral monitor 10 is installed or a supervisor (e.g., parent or guardian) of such person. Alternatively, some or all of the image and sensor data processing and report generation described above can be performed by a computing system remote to the oral monitors 10, which remote system can receive image and sensor data from the oral monitors 10. Such remote system can include for example a wireless communication device 30 which by a processor implements an application to process image and sensor data received from the oral monitor 10 and/or generate reports based on such data. Such remote system can alternatively include one or more network connectable servers 50 accessible through one or more networks 40 (e.g., the Internet and mobile carrier networks).

The server 50 or wireless communication devices 30 can transmit notifications including reports generated based on processed image and/or sensor data to computing devices 60 such as mobile communication devices, personal computers, and email and messaging servers. Notifications can be transmitted as emails, short message service (SMS) messages, multimedia messaging service (MMS), or other messaging or reporting protocol for example a protocol enabled by an oral monitoring application installed on a computing device 60. The devices 60 can correspond to the person in whose mouth 2 the oral monitor 10 is installed. Devices 60 can alternatively correspond to a person who is charged with supervision of the person in whose mouth 2 the oral monitor 10 is installed, for example a parent or guardian of a child in whose mouth 2 the oral monitor 10 is installed.

Figure 7:
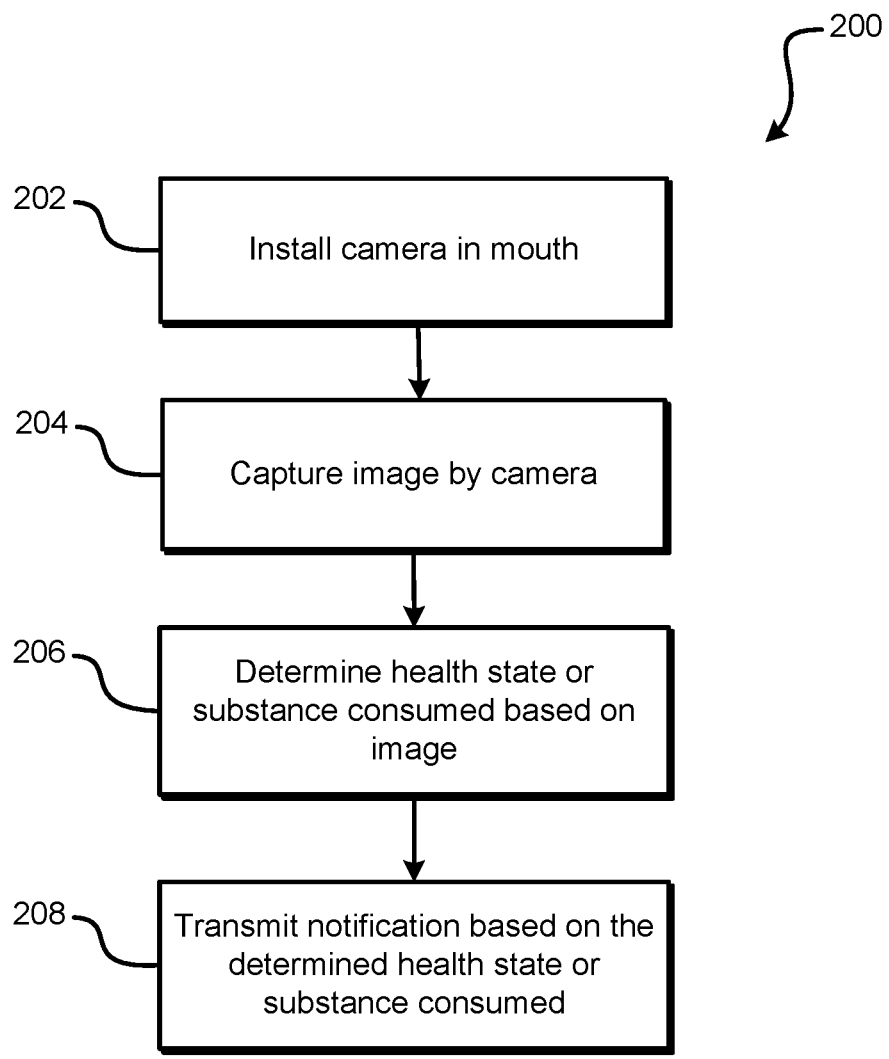
FIGS. 7 and 8 are flow charts showing oral monitoring methods.

Referring to FIG. 7, a flowchart shows a method 200 performed by the oral monitor 10 via the CPU 106. While the method 200 and associated processes are described with reference to the components shown in FIGS. 1 and 6, including the oral monitor 10 and associated hardware 102, the method 200 may alternatively be performed via other suitable system or systems. In a step 202 a camera 116 is installed in a mouth 2 of a user. In a step 204 one or more images are captured by the camera 116. In a step 206, a processor determines a health state of the mouth and/or a substance consumed by the user based on the one or more images captured. In a step 208, a notification is transmitted to a user based on the determined health state and/or substance consumed. Alternatively, a chemical sensor 108 can be installed in the mouth 2 and the health state and/or substance (e.g., food sugar) consumed can be determined based on image data from the camera 116 and/or data from the chemical sensor 108. The user to whom the notification is transmitted can correspond to a person in whose mouth 2 the oral monitor 10 is installed, or alternatively a supervisor (e.g., parent or guardian) of such person.

Figure 8:
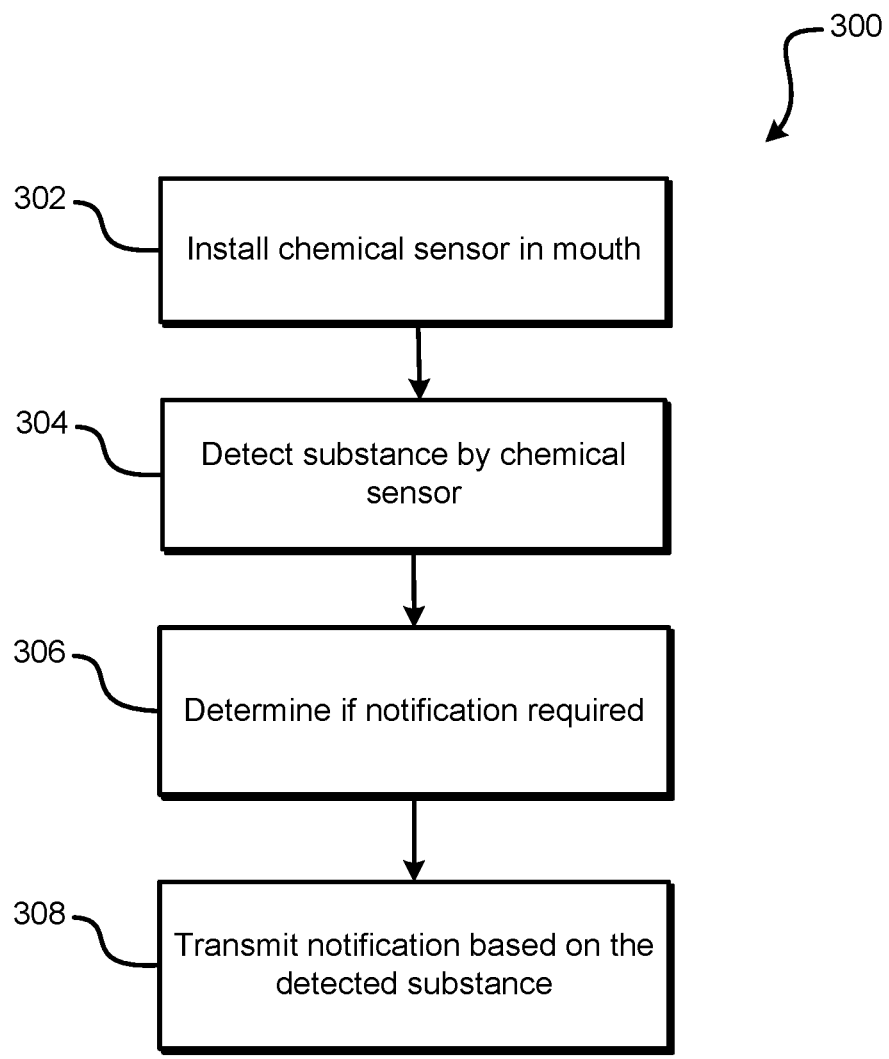

Referring to FIG. 8, a flowchart shows a method 300 performed by the oral monitor 10 via the CPU 106. While the method 300 and associated processes are described with reference to the components shown in FIGS. 1 and 6, including the oral monitor 10 and associated hardware 102, the method 300 may alternatively be performed via other suitable system or systems. In a step 302 a chemical sensor 108 is installed in a mouth of a user. In a step 304 a substance (e.g., a food sugar) is detected by the chemical sensor 108. In a step 306, a processor determines if a notification is required based on the detected substance. In a step 308, a notification is transmitted to a user based on the detected substance. The user to whom the notification is transmitted can correspond to a person in whose mouth 2 the oral monitor 10 is installed, or alternatively a supervisor (e.g., parent or guardian) of such person.

Although features and elements are described above in particular combinations, one of ordinary skill in the art will appreciate that each feature or element can be used alone or in any combination with the other features and elements. Methods described herein may be implemented in a computer program, software, or firmware incorporated in a computer-readable medium for execution by a computer or processor.

While embodiments have been described in detail above, these embodiments are non-limiting and should be considered as merely exemplary. Modifications and extensions may be developed, and all such modifications are deemed to be within the scope defined by the appended claims.

What is claimed is:

1. An oral monitoring method comprising:
providing an oral monitor comprising a camera, a memory capable of image storing, at least one processor, and a wireless transmitter that operates under a wireless Ethernet protocol;
adhering the oral monitor to a first tooth in a mouth;
capturing a plurality of images by the camera over a period of time;
determining by the at least one processor based on at least one of the plurality of images captured a health state of the mouth comprising an amount of plaque on a second tooth in line with the first tooth in the mouth and at least one of a number of times a particular substance is consumed by the mouth or a number of times a particular activity is performed by the mouth; and
transmitting by the wireless transmitter via the wireless Ethernet protocol a notification based on the amount of plaque on the second tooth in the mouth and based on the at least one of the number of times the particular substance is consumed or the number of times the particular activity is performed by the mouth.

2. An oral monitoring method comprising:
providing at least one camera and at least one chemical sensor;
attaching the at least one camera and the at least one chemical sensor to a tooth in a mouth;
capturing a plurality of images by the at least one camera over a period of time;
detecting by the at least one chemical sensor a particular substance in the mouth;
determining by at least one processor based on the plurality of images captured and the detecting by the at least one chemical sensor a health state of the mouth comprising a number of times the particular substance is consumed by the mouth; and
transmitting via a wireless Ethernet protocol a notification to a user based on the number of times the particular substance is consumed by the mouth.

3. An oral monitoring system comprising:
at least one camera installed in a mouth by adhering to a tooth for capturing images over a period of time;
a memory configured for storing images;
at least one processor that processes images captured by the at least one camera to determine a health state of the mouth comprising at least one of a number of times a particular substance is consumed by the mouth or a number of times a particular activity is performed by the mouth; and
a wireless transmitter that operates under a wireless Ethernet protocol that transmits data corresponding to the captured images, the data corresponding to the captured images comprising a notification to a user based on the at least one of the number of times the particular substance is consumed by the mouth or the number of times the particular activity is performed by the mouth.

4. The oral monitoring system of claim 3, further comprising a housing attaching the oral monitoring system to an orthodontic apparatus connected to teeth in the mouth.

5. The oral monitoring system of claim 3, the at least one camera comprising:
a first camera positioned within the mouth facing outside of the mouth; and a second camera positioned within the mouth facing toward a cheek of the mouth.

6. The oral monitoring system of claim 3, wherein the wireless transmitter comprises a wireless transceiver that operates under the wireless Ethernet protocol.

7. The oral monitoring system of claim 3, further comprising:
a chemical sensor that detects food sugars in the mouth;
the at least one processor that further processes food sugar information collected by the chemical sensor; and
the wireless transmitter that transmits data corresponding to the food sugar information.

8. The oral monitoring system of claim 3, the at least one processor further determines tooth brushing based on the images captured by the at least one camera.

9. The oral monitoring system of claim 8, wherein the at least one processor applies a classifier to the images captured to determine the tooth brushing.

10. The oral monitoring system of claim 3, the at least one camera capturing images of teeth in the mouth, the at least one processor further determining based on the captured images at least one of an amount of plaque, a formation of a cavity, a formation of an abscess, or a dental anomaly in the mouth.

11. The oral monitoring system of claim 10, the at least one processor further:
determining based on the images captured when a medical anomaly occurs within the mouth; and
transmitting the notification responsive to determining the medical anomaly.

12. The oral monitoring system of claim 10, the at least one processor further:
determining based on the images captured when a threshold amount of plaque has accumulated on teeth within the mouth; and
transmitting the notification responsive to determining the threshold amount of plaque has accumulated.

13. The oral monitoring system of claim 3, the at least one camera capturing images of consumption in the mouth, the at least one processor further:
determining consumption activities based on the captured images;
generating a report based on the consumption activities; and
transmitting the report to the user.

14. The oral monitoring system of claim 13, further comprising a chemical sensor that detects food sugars, the at least one processor further:
determining based on the captured images and based on detected food sugars a quality of food consumed in the mouth; and
generating the report to comprise an indication of the quality of the food consumed in the mouth.

15. The oral monitoring system of claim 3, the at least one camera capturing images of smoke in the mouth, the at least one processor:
determining based on the captured images smoking activity; and
generating a report comprising an indication of the smoking activity.

16. The oral monitoring system of claim 3, further comprising a chemical sensor that detects at least one particular mind altering substance consumed in the mouth, the at least one processor further generating a report comprising an indication of the at least one particular mind altering substance.

17. The oral monitoring system of claim 16, wherein the at least one particular mind altering substance comprises an illicit drug.

18. The oral monitoring system of claim 16, wherein the at least one particular mind altering substance comprises at least one of alcohol or marijuana.

19. The oral monitoring system of claim 3, further comprising a network connected server, the at least one processor comprising a particular processor of the server, the server:
receiving the data transmitted from the wireless transmitter;
determining by the particular processor of the server the health state of the mouth comprising the at least one of the number of times the particular substance is consumed by the mouth or the number of times the particular activity is performed by the mouth; and
transmitting the notification to the user.

20. The oral monitoring system of claim 3, wherein the at least one camera comprises a video camera.

21. The oral monitoring system of claim 3, the system further comprising:
a housing comprising the at least one camera, the memory, and the at least one processor; and
an adhesive for adhering the housing to a surface of the tooth.

22. An oral monitoring method comprising:
providing at least one camera;
attaching the at least one camera to a tooth in a mouth;
capturing a plurality of images by the at least one camera over a period of time;
determining by at least one processor based on the plurality of images captured a health state of the mouth comprising at least one of a number of times a particular substance is consumed by the mouth or a number of times a particular activity is performed by the mouth; and
transmitting via a wireless Ethernet protocol a notification to a user based on the determined at least one of the number of times the particular substance is consumed by the mouth or the number of times the particular activity is performed by the mouth.

23. The method of claim 22, further comprising:
providing a chemical sensor;
attaching the chemical sensor in the mouth;
detecting by the chemical sensor the particular substance in the mouth;
determining further based on the detecting by the chemical sensor the number of times the particular substance is consumed by the mouth; and
transmitting the notification to the user further based on the detecting by the chemical sensor of the particular substance in the mouth.

24. The method of claim 23, further comprising determining the number of times the particular activity is performed further based on the detecting by the chemical sensor of the particular substance.

25. The method of claim 23, further comprising:
determining by the chemical sensor an amount of food sugar in the particular substance; and
classifying the particular substance based on the amount of food sugar;
wherein the transmitted notification comprises an indication of the classification of the particular substance.

26. The method of claim 25, further comprising determining a number of times the classified detected particular substance was consumed, wherein the transmitted notification comprises an indication of the number of times the classified detected particular substance was consumed.

27. The method of claim 23, further comprising providing the at least one camera and the chemical sensor in a housing and adhering the housing to a surface of the tooth.

28. The method of claim 22, further comprising:
providing a chemical sensor;
attaching the chemical sensor in the mouth;
detecting by the chemical sensor a food sugar in the mouth; and
transmitting the notification to the user further based on the detected food sugar in the mouth.

29. The method of claim 22, wherein the mouth is that of a first person and the user is a second person who supervises the first person.

30. The method of claim 22, wherein the particular activity is eating.

31. The method of claim 22, wherein the particular activity is teeth brushing.

32. The method of claim 22, wherein attaching the camera in the mouth comprises adhering the camera to an outside surface of the tooth.

33. The method of claim 22, wherein attaching the at least one camera in the mouth comprises attaching the at least one camera to an orthodontic apparatus connected to teeth in the mouth.

34. The method of claim 22, wherein attaching the at least one camera in the mouth comprises attaching the at least one camera on the tooth and facing outside of the mouth.

35. The method of claim 22, wherein the particular activity performed is smoking.

36. An oral monitoring method comprising:
providing at least one camera;
providing at least one chemical sensor;
attaching the at least one camera and the at least one chemical sensor to a tooth in a mouth;
detecting a substance by the at least one camera and the at least one chemical sensor;
determining by the chemical sensor an amount of food sugar in the substance;
classifying the detected substance based on the amount of food sugar;
determining a health state of the mouth comprising a number of times the classified detected substance was consumed by the mouth;
determining a notification by at least one processor based on the classified detected substance, the notification comprising an indication of the number of times the classified detected substance was consumed by the mouth; and
transmitting via a wireless Ethernet protocol the notification to a user.

37. The method of claim 36, further comprising transmitting the notification responsive to determining that a threshold number of times the classified detected substance was consumed has been reached.

38. An oral monitoring method comprising:
providing an oral monitor comprising a camera, a memory that stores images, at least one processor, and a wireless transmitter that operates under a wireless Ethernet protocol;
adhering the oral monitor to a surface of a tooth in a mouth;
capturing a plurality of images by the camera over a period of time;
determining by the at least one processor based on the plurality of images captured a health state of the mouth comprising a number of times a particular substance is consumed by the mouth; and
transmitting by the wireless transmitter via the wireless Ethernet protocol a notification based on the number of times the particular substance is consumed by the mouth.

* * * * *